United States Patent [19]

Zaiger

[11] Patent Number: Plant 6,024

[45] Date of Patent: Sep. 29, 1987

[54] NECTARINE TREE 51G110S

[76] Inventor: Chris F. Zaiger, 537 Rosemore Ave., Modesto, Calif. 95351

[21] Appl. No.: 809,137

[22] Filed: Dec. 16, 1985

[51] Int. Cl.[4] ..... A01H 5/03

[52] U.S. Cl. ..... Plt./41

[58] Field of Search ..... Plt. 41

*Primary Examiner*—Robert E. Bagwill

[57] ABSTRACT

A new variety of nectarine tree which is of large size, vigorous, upright in growth, the tree being a regular and productive bearer of large size, yellow flesh, clingstone fruit with good eating quality. The fruit is further characterized by its high degree of red skin color, its firm flesh with good storage quality and its ability to ship to long distance markets.

1 Drawing Figure

ORIGIN OF THE VARIETY

The new variety of nectarine tree was developed by me in my experimental orchard, located at Modesto, Calif., as a second generation seedling from a cross between May Grand Nectarine (U.S. Plant Pat. No. 2,794) and a seedling which originated from a group of seedlings grown from open pollinated Red Grand Nectarine (U.S. Plant Pat. No. 1,060) seed.

ASEXUAL REPRODUCTION OF THE VARIETY

The new variety of nectarine tree was asexually propagated by budding, as performed by me at Modesto, Calif. and shows that said characteristics are established and transmitted through succeeding propagations and run true to the original tree in all respects.

SUMMARY OF THE INVENTION

The new and distinct variety of nectarine tree is of large size, upright in growth and a regular and productive bearer of large size, early maturing, yellow flesh, clingstone fruit. The fruit is further characterized by having a high degree of red skin color, firm flesh, and the ability to ship to long distance markets. The present variety of nectarine tree when compared to May Grand Nectarine (U.S. Plant Pat. No. 2,794) bears fruit which matures 5–6 days earlier, has more uniform size fruit throughout the tree, especially on the smaller fruit bearing wood in the lower portion of the tree.

PHOTOGRAPHS OF THE VARIETY

The accompanying photographs show typical specimens of the foliage and fruit of my new variety of nectarine tree, a section of a small branch with the upper and lower surface of the leaves being illustrated. An exterior view of the fruit is shown with a fruit divided in its suture plane to reveal flesh coloration and showing a stone remaining in place. The photographs were taken shortly after being picked at maturity (shipping ripe) and the colors are as nearly true as reasonably possible in a color representation of this type.

DESCRIPTION OF THE VARIETY

The following is a botanical description of the new variety of nectarine tree and its flowers, foliage and fruit based on observations of specimens grown at Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Production.*—Productive.
- *Density.*—Medium dense.
- *Bearing.*—Regular.

Trunk:
- *Size.*—Medium stocky.

Branches:
- *Size.*—Medium stocky.
- *Texture.*—Medium rough.
- *Lenticels.*—Medium size. Medium number.

Leaves:
- *Size.*—Average length—7″. Average width—1¾″.
- *Form.*—Lanceolate.
- *Margin.*—Crenate.
- *Color.*—Upper surface—green to dark green (29-F-5) to (29-F-8). Lower surface—dull green to grayish green (29-E-6) to (29-E-8).
- *Texture.*—Smooth.

*Petiole.*—Medium length. Medium thickness.

*Glands.*—Number varies from 2 to 4. Average number 2. Reinform. Located on base of leaf and upper portion of petiole.

Flower buds:

Size.—Medium.

*Length.*—Medium.

Flowers:

*Blooming period.*—Mar. 2, 1984 to Mar. 12, 1984. Varies slightly with climatic conditions.

*Size.*—Large, showy.

Fruit:

*Maturity when described.*—Firm ripe.

*Date of first picking.*—June 7, 1984.

*Date of last picking.*—June 12, 1984.

*Size.*—Large. Comparatively uniform. Average diameter axially — 2 7/16". Average transversely in suture plane — 2 7/16".

*Form.*—Globose, nearly symmetrical.

*Suture.*—Shallow, extends from base to apex.

*Apex.*—Varies from round to slight apexial point.

*Ventral surface.*—Rounded, slightly lipped.

*Cavity.*—Rounded. Average depth — 7/16". Average breadth — ¾".

Skin:

*Thickness.*—Medium.

*Texture.*—Medium, tenacious to flesh.

*Tendency to crack.*—None.

*Down.*—Wanting.

*Color.*—Bright yellow ground color (4-A-6) to (4-A-8). Red blush covering most of the surface exempt portions of stem cavity (9-A-8) to (10-B-8).

Flesh:

*Texture.*—Firm, meaty.

*Juice.*—Moderate.

*Amygdalin.*—Undetected.

*Ripens.*—Uniform.

*Flavor.*—Very slightly acid to sub-acid.

*Aroma.*—Very little.

*Eating quality.*—Good.

*Fibers.*—Few and tender.

*Color.*—Yellow to golden yellow (4-A-6) to (5-A-6).

Stone:

*Type.*—Clingstone.

*Size.*—Large. Average length — 1½". Average breadth — 1⅛". Average thickness — ¾".

*Form.*—Obovate — tip varies from rounded to cuspidate.

*Base.*—Straight to slightly rounded.

*Sides.*—Mostly equal.

*Surface.*—Irregularly furrowed toward apex, usually pitted toward base.

*Color.*—Light brown (7-B-5) to (8-C-6).

*Tendency to split.*—Very slight.

Use: Dessert.

*Market.*—Local and long distance.

Storage quality: Good.

Shipping quality: Good.

The nectarine tree and its fruit herein described may vary in slight detail due to climatic, soil conditions and cultural practices under which the variety may be grown; the present description being that of the variety as grown by me in my experimental orchard at Modesto, Calif.

I claim:

1. A new and distinct variety of nectarine tree, substantially as illustrated and described, characterized by its large size, vigorous, upright growth, a productive and regular bearer of large size, firm, yellow flesh, clingstone fruit with attractive red skin color and good eating quality; the tree is further characterized in comparison with May Grand Nectarine (U.S. Plant Pat. No. 2,794) by producing fruit that ripens 5 to 6 days earlier and being able to produce fruit with more uniform size throughout the tree, especially on smaller fruiting wood in the lower portion of the tree.

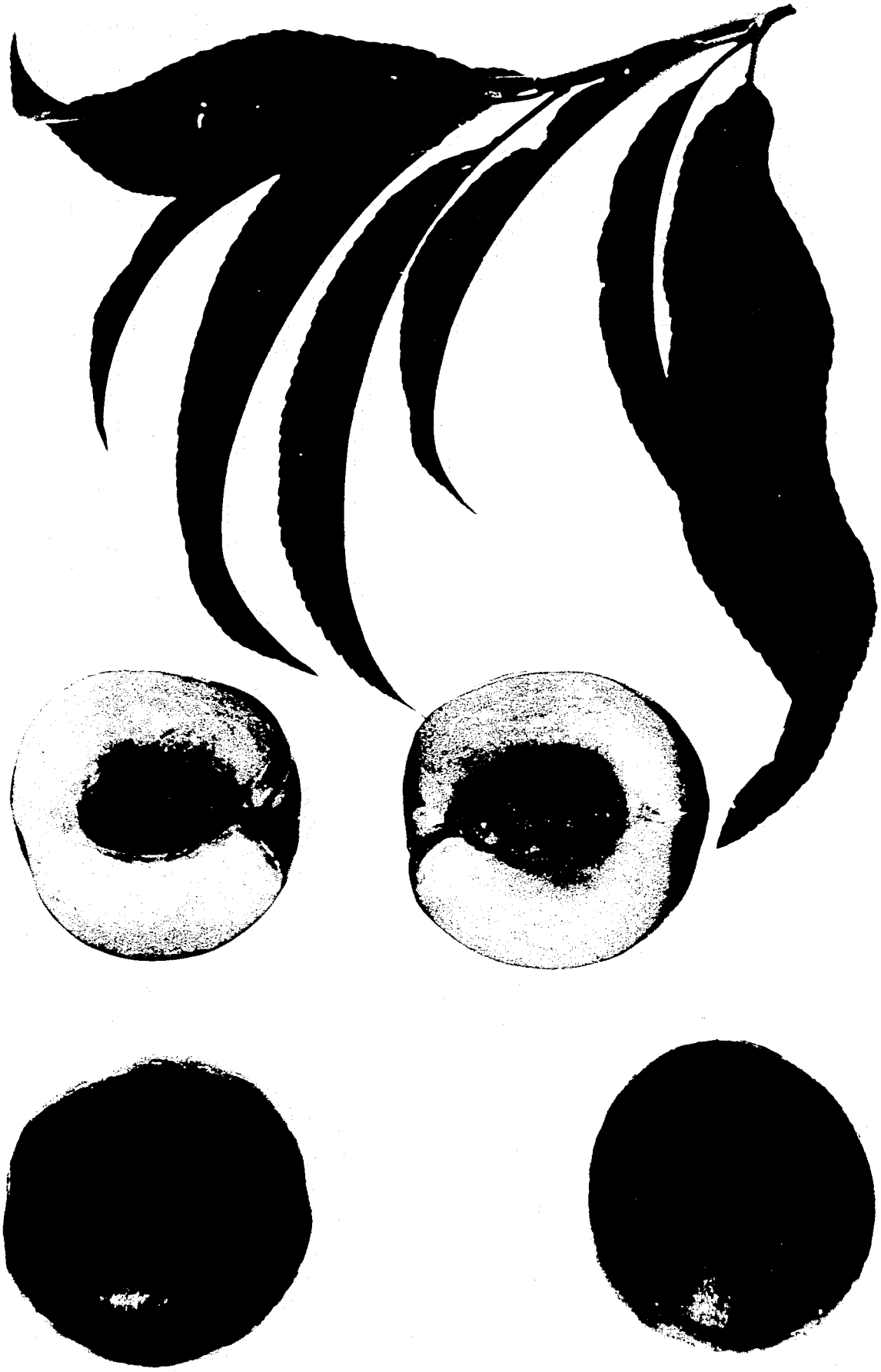

* * * * *